United States Patent [19]

Bencze et al.

[11] 4,212,536
[45] Jul. 15, 1980

[54] HOLOGRAPHIC SUBTRACTION WITH PHASE MODULATION TO DISTINGUISH PHASE AND AMPLITUDE DIFFERENCES

[75] Inventors: György Bencze; András Hamori, both of Budapest, Hungary

[73] Assignee: Magyar Tudományos Akadémia Központi Fizikai Kutató Intezéte, Budapest, Hungary

[21] Appl. No.: 839,606

[22] Filed: Oct. 5, 1977

Related U.S. Application Data

[63] Continuation-in-part of Ser. No. 798,451, May 19, 1977, abandoned.

[30] Foreign Application Priority Data

May 31, 1976 [HU] Hungary ................................. 2783

[51] Int. Cl.² .................. G06K 9/08; G01B 9/027; G03H 1/16; G03H 1/28
[52] U.S. Cl. .................................. 356/71; 350/3.6; 350/3.77; 350/3.83; 350/3.86; 356/347
[58] Field of Search ............... 350/3.6, 3.67, 3.75, 350/3.77, 3.83, 3.85, 3.86, 347; 356/71, 109

[56] References Cited

U.S. PATENT DOCUMENTS

| | | | |
|---|---|---|---|
| 3,537,854 | 11/1970 | Grobin et al. ................. | 350/3.86 |
| 3,627,426 | 12/1971 | Tsuryta et al. ................ | 356/109 |
| 3,729,634 | 4/1973 | Jensen et al. .................. | 350/3.6 |
| 3,767,285 | 10/1973 | Mezrich ........................ | 350/3.86 |
| 3,826,555 | 7/1974 | Matsumoto .................... | 350/3.6 |
| 4,024,513 | 5/1977 | Huignard et al. .............. | 350/3.83 |

OTHER PUBLICATIONS

Neumann et al., *Applied Optics*, vol. 6, No. 6, Jun. 1967, pp. 1097-1104.
Bruning et al., *IEEE Transactions on Electron Devices*, vol. ed-22, No. 7, Jul. 1975, pp. 487-495.
Watkins, *Applied Optics*, vol. 12, No. 8, Aug. 1973, pp. 1880-1884.
Bromley et al., *Applied Optics*, vol. 10, No. 1, Jan. 1971, pp. 174-181.

*Primary Examiner*—Ronald J. Stern
*Attorney, Agent, or Firm*—Karl F. Ross

[57] ABSTRACT

Two substantially identically patterned transparencies, i.e. a master photomask and a copy thereof, are compared with each other by transluminating the master with an object beam, producing a hologram of that master by letting the object beam interfere with a reference beam from a common source of coherent light such as a laser, placing the copy in the path of the object beam formerly occupied by the master, and positioning the developed hologram at the intersection of the two beams to generate a compound beam of zero intensity if the two transparencies are identical. The luminous energy of the compound beam thus varies inversely with the degree of equivalency of the two transparencies. The compound beam may be imaged onto a receiving surface, with certain areas thereof blocked out to eliminate error indications from insignificant (e.g. marginal) zones.

10 Claims, 5 Drawing Figures

HOLOGRAPHIC SUBTRACTION WITH PHASE MODULATION TO DISTINGUISH PHASE AND AMPLITUDE DIFFERENCES

CROSS-REFERENCE TO RELATED APPLICATION

This application is a continuation-in-part of our copending application Ser. No. 798,451 filed May 19, 1977 and now abandoned.

FIELD OF THE INVENTION

Our present invention relates to a method of and an apparatus for detecting errors on a photomask with respect to a standard photomask by subtraction technique. Such photomasks can preferably be used in the production of integrated circuits or the like, e.g. of magnetic bubble memories.

BACKGROUND OF THE INVENTION

In the conventional production of integrated circuits a semiconductor substrate is coated with a layer of photoresist and then illuminated through a special photographic plate, the so-called photomask. The photoresist is then developed, as by the removal of its exposed portions and the processing of the underlying semiconductor substrate, e.g. by etching. The photomask contains patterns consisting of a number of lines and various geometrical figures. In most cases, the pattern is divided into several identical configurations—known in the industry as mask elements—each associated with a separate circuit. Mask elements are generally produced by photographic technique, including multiple reduction. The photomasks containing a plurality of mask elements are produced by a high-accuracy step-and-repeat technique using a special camera.

Since this way of producing photomasks is both expensive and time-consuming, it is desirable to exploit the individual photomasks to a maximum extent. Moreover, damaged photomasks have to be withdrawn from production as their use would otherwise result in improperly functioning integrated circuits. To satisfy the extreme resolution requirements of modern integrated circuits, industrial practice uses contact copying of the photomasks both for their reproduction and for their transfer to the photoresist-coated wafer. During contact copying the photomasks touch each other and the photoresist-coated semiconductor, thereby risking damage or contamination. Already during the production of photomasks there may arise defects such as scratches, bubbles, microscopic holes or the like. Consequently, there is a great need for inspecting photomasks to determine whether or not they meet existing requirements.

Besides conventional microscopic testing, methods using coherent illumination are known for inspecting photomasks employed in IC production; see, for example, U.S. Pat. Nos. 3,743,423 and 3,787,117. In one such method, based upon intensity (spatial) filtering, the photomask is illuminated by a spatially coherent light beam which is diffracted when penetrating the photomask. The diffracted light is focused by a lens onto a planar optical spatial filter consisting of discrete opaque areas on a transparent field. The distance between the opaque areas is inversely proportional to the distance between the elements on the photomask. The filter spatially modulates the incident diffraction pattern and suppresses the periodic signal component. The light so modulated is retransformed to yield an image which contains no periodic signal and, consequently, shows an intensity distribution corresponding to the random pattern of defects in the photomask.

The techniques employing intensity (spatial) filtering have the following disadvantages:

(a) only randomly distributed, nonperiodic errors can be detected;

(b) they are effective only if the inspected photomasks contain a large number of elements;

(c) they also detect errors when phase defects are found which do not influence the quality of the manufacturing process.

Another method using coherent illumination utilizes subtractive spatial filtering for inspecting photomasks. A beam of coherent radiation is directed onto the photomask to be modulated and is then passed through a mask containing at least two apertures aligned with the columns of the matrix-like array of photomask elements. Both the aperture widths and the aperture-to-aperture spacing are functions of the element-to-element spacing along the rows of the array. The beam traversing the apertured mask is passed through a lens and then through an optical grating positioned in the focal plane of that lens. The grating has rulings parallel to the major axis of the apertures and is asymmetrical with respect to the optical axis. The grating periodicity is a function of the element-to-element spacing along the rows of the array. Finally, the resulting central and side images of each aperture are displayed on a receiving surface. The centermost side images of each aperture overlap and cancel each other and, hence, the nonperiodic errors of the photomask can be detected.

Accordingly, the disadvantages of this latter method can be summarized as follows:

(a) As the described technique mainly utilizes those parts of the optical elements which lie at a distance from the optical axis, the deviations due to lens aberration, uneven illumination etc. assume added importance and are—erroneously—detected as defects of the photomask.

(b) The optical elements cannot be exploited sufficiently to be able to ensure a high resolution.

(c) The geometric arrangement does not allow comparison of the inspected photomask with a standard photomask because there is not enough space for the displacement of the photomask.

(d) The technique is suitable for the detection of randomly distributed, nonperiodic errors only.

(e) Phase defects in the photomask not detrimental to the production are also detected as errors.

A general disadvantage of the methods using subtractive spatial filtering is that the images to be subtracted arrive in the plane of detection along different optical paths. In practical applications, the inevitable small deviations between the individual optical paths due to, for example, lens aberrations are misinterpreted and detected as errors of the photomask.

OBJECTS OF THE INVENTION

The following problems are to be solved by our invention:

(1) The photomasks or the individual photomask elements should be able to be compared with a standard photomask or standard photomask elements. This would allow the detection of both random and periodic errors.

(2) The images of both the standard and the inspected photomask should be obtained by a beam arriving along the same optical path through the central, symmetrically situated parts of the optical elements.

(3) The optical elements should be able to be maximally exploited.

(4) A distinction should be made between amplitude and phase errors.

(5) The inspection of photomasks should be unaffected by the member of the elements contained therein.

(6) A basis should be established for the implementation of an automatic photomask-inspecting system.

SUMMARY OF THE INVENTION

Our invention is based on recognition of the fact that holography, when combined with the subtraction technique, furnishes a very accurate means of error detection for inspecting photomasks. The advantages of this solution are particularly noteworthy in the production of integrated circuits, magnetic bubble memories or the like.

When an object is illuminated, the light diffracted therefrom carries information about its structure. This information is carried by the phase and the amplitude of the light wave or, in other words, by its complex wave function. Thus, in order to record the complete information available from the object, not only amplitude but also phase should be registered. Since conventional methods, like photography, are capable of detecting intensity only, the phase information is lost in such a recording.

This problem can be solved by holography. In this method, a wave emitted by a source of coherent light and modulated by the object is made to interfere with another, so-called reference wave from the same source and the resulting interference pattern is photographically recorded. Since the phases of the two waves also participate in the formation of the interference pattern, this method includes also an indirect phase recording.

Another significant advantage of holography follows from the above-mentioned properties of the diffracted light, namely, the fact that light diffracted from each point of the object arrives in each point of the recording medium, which means that any small part of the latter contains information concerning the whole object. Consequently, a minor damage of the recording plate does not cancel any useful information; it can, at worst, only degrade the quality of the information.

Usually, the holographic recording material is a photographic plate but other sensitive media can also be used.

Exposure to the interference image and the following treatment modify the transmission and reflection properties of the recording medium (photoplate) in accordance with the distribution of the intensity of exposure. The recording obtained in this way is called a hologram. If a developed hologram is illuminated by the reference beam used for the exposure, a part of the light will reconstruct the beam coming from the object during exposure.

One of the conditions of the interference is the strict coherence of the individual beams; a laser is the most suitable light source currently available.

BRIEF DESCRIPTION OF THE DRAWING

The above and other features of our invention will now be described in detail with reference to the accompanying drawing showing some exemplary embodiments. In the drawing.

SPECIFIC DESCRIPTION

Figure 1:
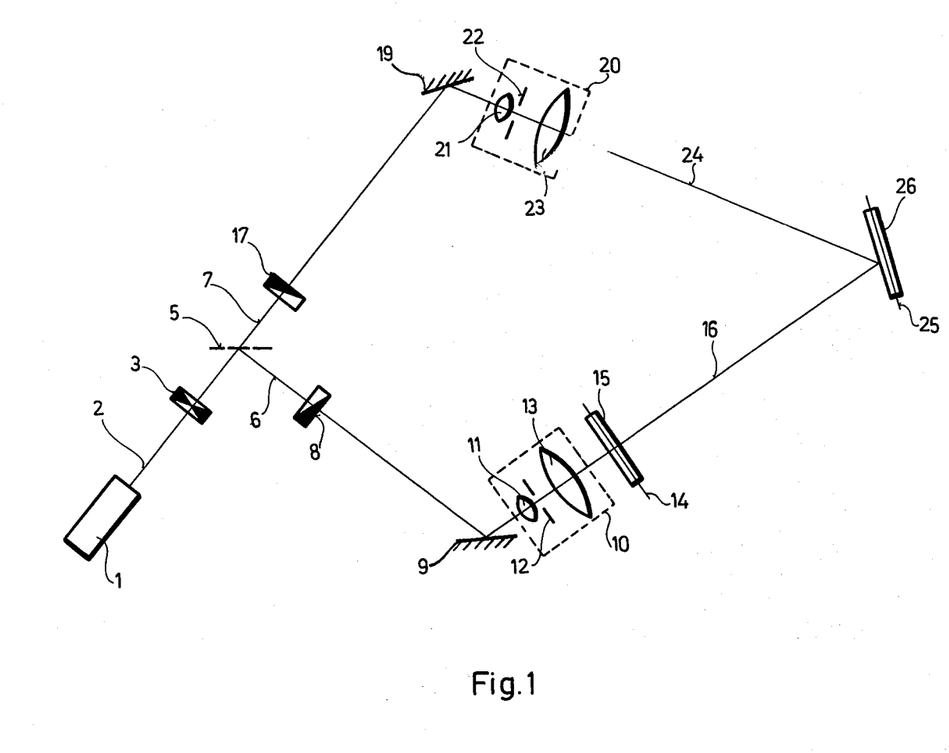
FIG. 1 is a schematic view of a holographic recording system.

The arrangement shown in FIG. 1 is designed to record a standard hologram. An undivided coherent beam 2 emitted by a coherent-light source 1 such as a laser passes through an open electromechanical shutter 3 and is then partially reflected by a beam splitter 5. The reflected illuminating beam 6 passes through a beam attenuator 8 and is then directed by a deflector 9 to an afocal beam expander 10 consisting of a positive first lens 11, a spatial filter 12 in the shape of a diaphragm and a positive second lens 13. The beam expander 10 projects the Fourier transform of the illuminating beam onto the secondary focal plane of the first lens 11 having a short focal length. If the illuminating beam 6 were an ideal plane wave, then its Fourier transform would fall on the intersection of that secondary focal plane with the axis of lens 11. Any disturbance in the illuminating beam 6 results in plane waves deviating from the direction of the axis (components of other spatial frequencies) which, after focusing by the lens 11, fall on different points of its focal plane. If, now, a spatial filter 12 with a circular aperture of suitable diameter is positioned in the focal plane of lens 11, the axial plane-wave component of the illuminating beam 6 will pass through this aperture, but all the other components will be blocked out by the spatial filter 12. The second lens 13 has a greater focal length so that the beam expander 10 widens the beam 6 at a rate proportional to the ratio of the two focal lengths. With a sufficiently high beam intensity the second lens 13 can be omitted and in that case an object plane 14 downstream of expander 10 will be illuminated by a divergent radiation starting from the spatial filter 12. The beam extended to the desired size illuminates a standard photomask 15 positioned in the object plane 14 and held by a frame not shown. After passing through the standard photomask 15, the beam 6 arrives at a hologram plane 25 as a modulated standard object beam 16. An undeflected reference beam 7 passes through the beam splitter 5 and then through a beam attenuator 17 and, after redirection by a deflector 19, arrives in a second beam expander 20 also consisting of a positive first lens 21, a spatial filter 22 and a positive second lens 23. This second beam expander 20 is identical in both construction and operation with the first beam expander 10. The beam extended to the desired size arrives, in an analogous manner, at the hologram plane 25 as a reference beam 24.

The two beams, i.e. the standard object beam 16 and the reference beam 24, arriving in the hologram plane 25 interfere with each other. To record the standard hologram, a holographic recording medium 26 (e.g. a photoplate) also mounted in a frame is placed in the hologram plane 25. The intensity value required by the properties of the holographic recording medium 26 can be adjusted with the beam attenuators 8 and/or 17. The holographic record is then taken by opening the electromechanical shutter 3 for a suitably chosen exposure time. A finished standard hologram 30 (see FIG. 2) is obtained by the necessary treatment—such as development and fixing—of the holographic recording medium 26.

Figure 2:
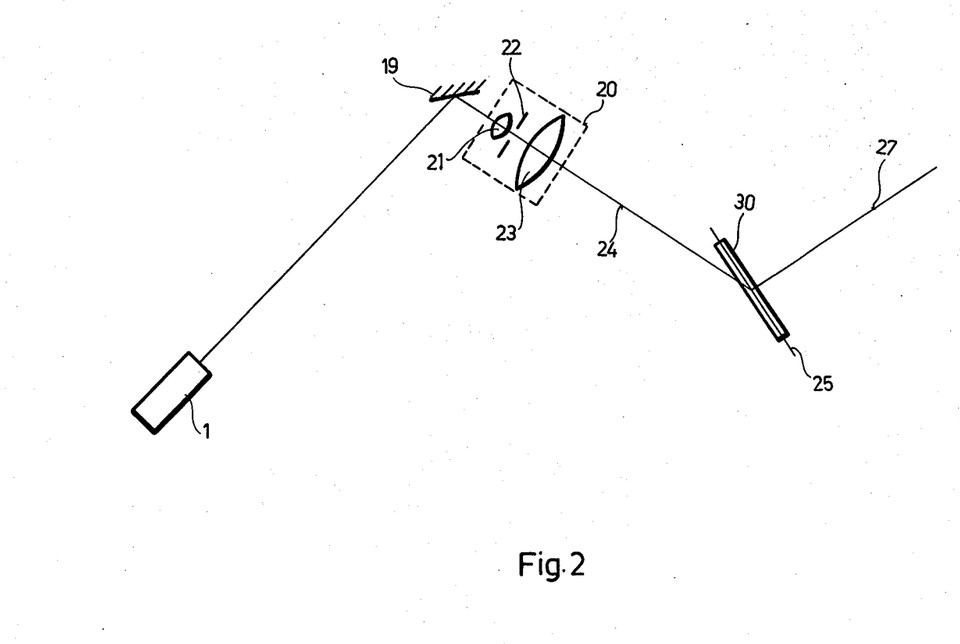
FIG. 2 is a schematic view of a complementary system for obtaining the reconstructed standard beam.

The most important characteristic of the standard hologram 30 obtained in this way is that, when placed in the hologram plane 25 in the same arrangement as during recording and illuminated by the reference beam 24 in accordance with FIG. 2, it diffracts the reference beam 24 and yields a reconstructed standard beam 27. This reconstructed standard beam 27 corresponds to the standard beam 16, used for taking the standard hologram 30, concerning both amplitude and phase conditions (see FIG. 1).

Figure 3:
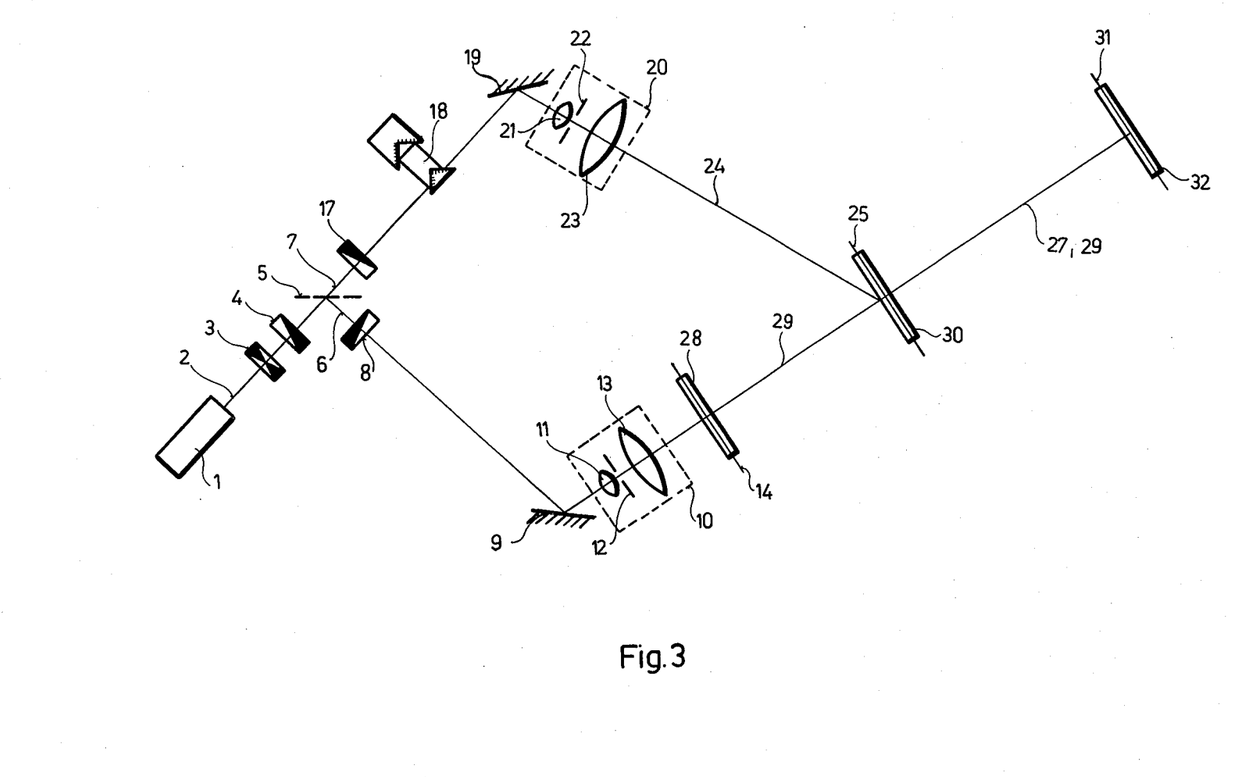
FIG. 3 is a view similar to FIG. 1, showing the system as used for practicing our invention.

An advantageous embodiment of a system for practicing our invention is illustrated in FIG. 3. The undivided coherent beam 2 emitted by the radiation source 1 passes through the open—e.g. electromechanical—shutter 3 and, after traversing an attenuator 4, is partly reflected by the beam splitter 5. The reflected beam 6 is deflected by the element 9—e.g. a mirror—and is then widened by the beam expander 10. The expanded beam transluminates a photomask 28 to be inspected which is located in the object plane 14. The modulated beam, after having passed through the photomask 28, serves as an analyzing object beam 29.

Figure 4:
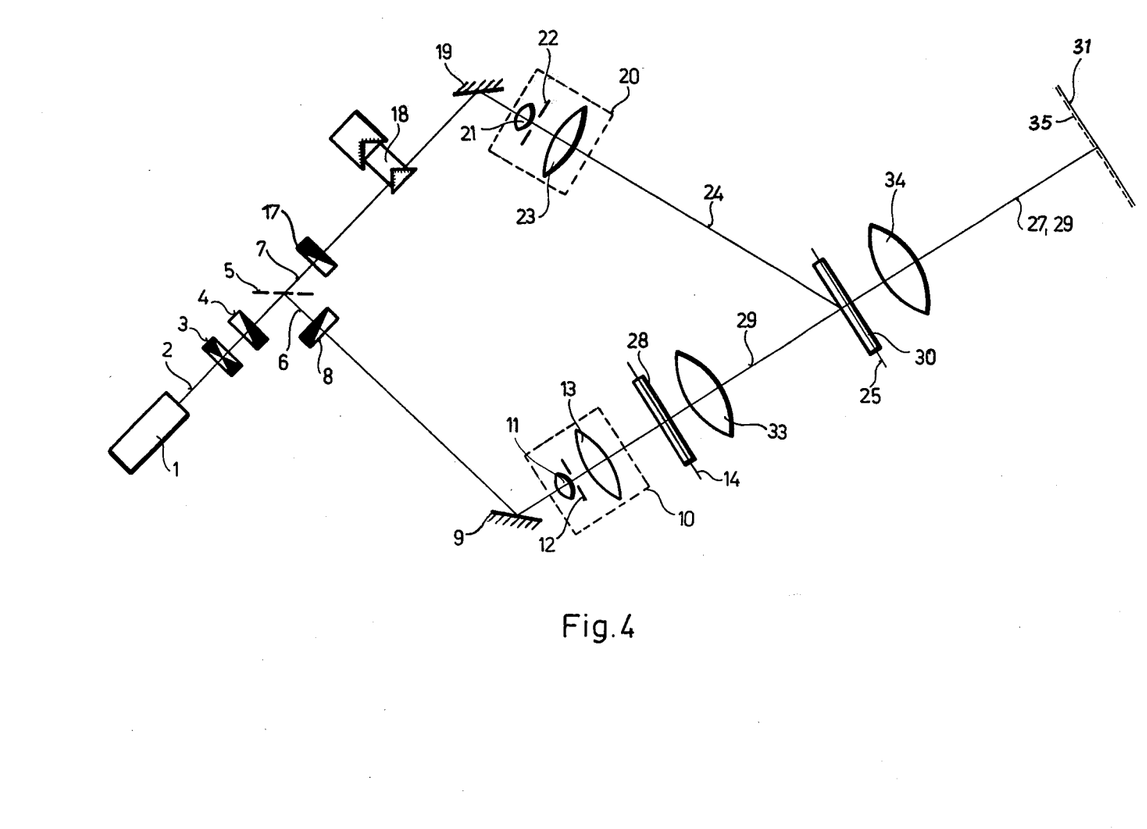
FIG. 4 is another view similar to FIG. 1, showing a modified system including image-forming elements.

The reference beam 7 passing through the beam splitter 5 is first deflected by the second mirror or similar element 19 and then widened by the beam expander 20. The beam thereupon arrives as reference beam 24 at the hologram plane 25. The reference beam 24 then reproduces the reconstructed standard beam 27 from the standard hologram 30. Downstream of the standard hologram 30 the analyzing object beam 29 and the reconstructed standard beam 27 interfere with each other and proceed as a compound beam 27, 29 along a common path to a beam detector 32 in a receiving plane 31. As illustrated in FIG. 4, a condensing lens 34 may be inserted ahead of the beam detector 32 (represented in this figure only by the plane 31) to concentrate the interfering rays onto the radiation-sensitive surface of that detector.

We shall now consider an arrangement which, as shown in FIG. 3, comprises the first beam attenuator 8 in the path of the object beam and the second beam attenuator 17 followed by a phase-difference controller 18 in the path of the reference beam, all located downstream of beam splitter 5. Let $f(x,y)$ and $g(x,y)$ denote the distribution of the complex wave function, in the receiving plane 31, of the analyzing object beam 29 and of the reconstructed standard beam 27, respectively, when the attenuation is at a minimum and the phase-difference controller 18 is set in its starting position. The receiving plane 31 lies behind the standard hologram 30 and is perpendicular to the direction of propagation of the radiation. The controller 18 adjusts the phase difference between the reconstructed standard beam 27 and the analyzing object beam 29 by varying the optical path length of one of these beams, here the beam 27.

Furthermore, let a and b denote the attenuation factors of the first and second beam attenuators 8 and 17, respectively, and $\phi$ be the phase difference between the reconstructed standard beam 27 and the analyzing object beam 29 as selected by the phase-difference controller 18. In this case the wave-function distribution $h(x,y)$ of the interference image obtained in the receiving plane 31 will be a linear combination of the distributions of the individual beams:

$$h(x,y) \sim a \cdot f(x,y) + b \cdot g(x,y) \cdot e^{i\phi}$$

By appropriate adjustment of the beam attenuators 8 and 17 as well as of the phase-difference controller 18, this distribution obtained in the receiving plane 31 can be made proportional to the differences between the standard photomask 15 (see FIG. 1) and the photomask 28 to be inspected (see FIG. 3). Hence, if the standard photomask 15 and the photomask 28 to be inspected are completely identical, the reconstructed standard beam 27 and the analyzing object beam 29 will completely cancel each other in the receiving plane 31. If, however, the inspected photomask 28 differs from the standard photomask 15 represented by hologram 30, then the cancellation in the receiving plane 31 will not be perfect and a beam intensity proportional to the differences can be detected in that plane 31. In this way, the defective and the flawless photomasks can be segregated by detecting the total radiation intensity present in receiving plane 31, i.e. by visual observation or with photoelectric measuring.

The differences between the inspected photomask 28 (FIG. 3) and the standard photomask 15 (FIG. 1), i.e. the errors, can be divided into two groups: amplitude errors and phase errors. Phase errors modulate the phase distribution of the penetrating beam whereas amplitude errors modulate its amplitude distribution.

The errors can further be classified according to whether or not they exert an influence on the performance of the finished integrated circuit. Phase errors in the photomasks are not disturbing. Nondisturbing errors are also the amplitude errors which occur at locations (e.g. along the margin) not relevant to the operation of the finished integrated circuits. To facilitate classification of the errors, the images of both the standard and the inspected photomasks should be formed in the receiving plane 31 whereby the difference image of these photomasks will be displayed.

In FIG. 4 we have shown the system of FIG. 3 supplemented by imaging elements designed for this purpose. When taking the standard hologram 30, the beam modulated by the standard photomask 15 passes through a first condenser lens 33 on its way to the hologram plane 25. During inspection, the beam modulated by the photomask 28 to be inspected proceeds along the same path. Both the reconstructed standard beam 27 and the analyzing object beam 29 arrive in the receiving plane 31 through a second condenser lens, namely the aforementioned lens 34, located downstream of the hologram plane 25. An appropriate choice of the positions and focal lengths of the first and second condenser lenses 33 and 34 can ensure that both the standard and the inspected photomasks are imaged in the plane 31 with a desired enlargement.

The focal lengths of the first and second condenser lenses 33 and 34, as well as their locations, uniquely determine the position of the receiving plane 31 and the attainable enlargement.

The image projection establishes a one-to-one correspondence between the points of the receiving plane 31 and those of the object plane 14. Thus, the determination of the location of the error signal on the difference image in plane 31 enables the decision of the error location in the examined photomask 28. Amplitude and phase errors are distinguished by providing a time-dependent phase difference between the reconstructed standard beam 27 and the analyzing object beam 29. This phase difference is obtained by continuously adjusting the phase-difference controller 18. Then the interference image h(x,y;t) in the receiving plane 31 changes in accordance with the varying phase difference:

$$h(x,y;t) \sim a \cdot f(x,y) + b \cdot e^{i\phi(t)} \cdot g(x,y)$$

where φ(t) is the time-dependent phase difference. If the difference between the standard photomask 15 (FIG. 1) and the inspected photomask 28 is of phase-error character only, then full cancellation can be attained in each point of the receiving plane 31 by appropriate adjustment of the phase difference. If an amplitude error is present, no total cancellation can be attained by the mere adjustment of the phase difference; thus, certain areas will remain illuminated by the compound beam 27, 29.

In order to eliminate the detection of amplitude errors from areas which cannot disturb the performance of the integrated circuit, an opaque covering mask 35 of suitable size can be positioned in the receiving plane 31 to overlie such areas. This covering mask can be designed together with the circuit.

Figure 5:
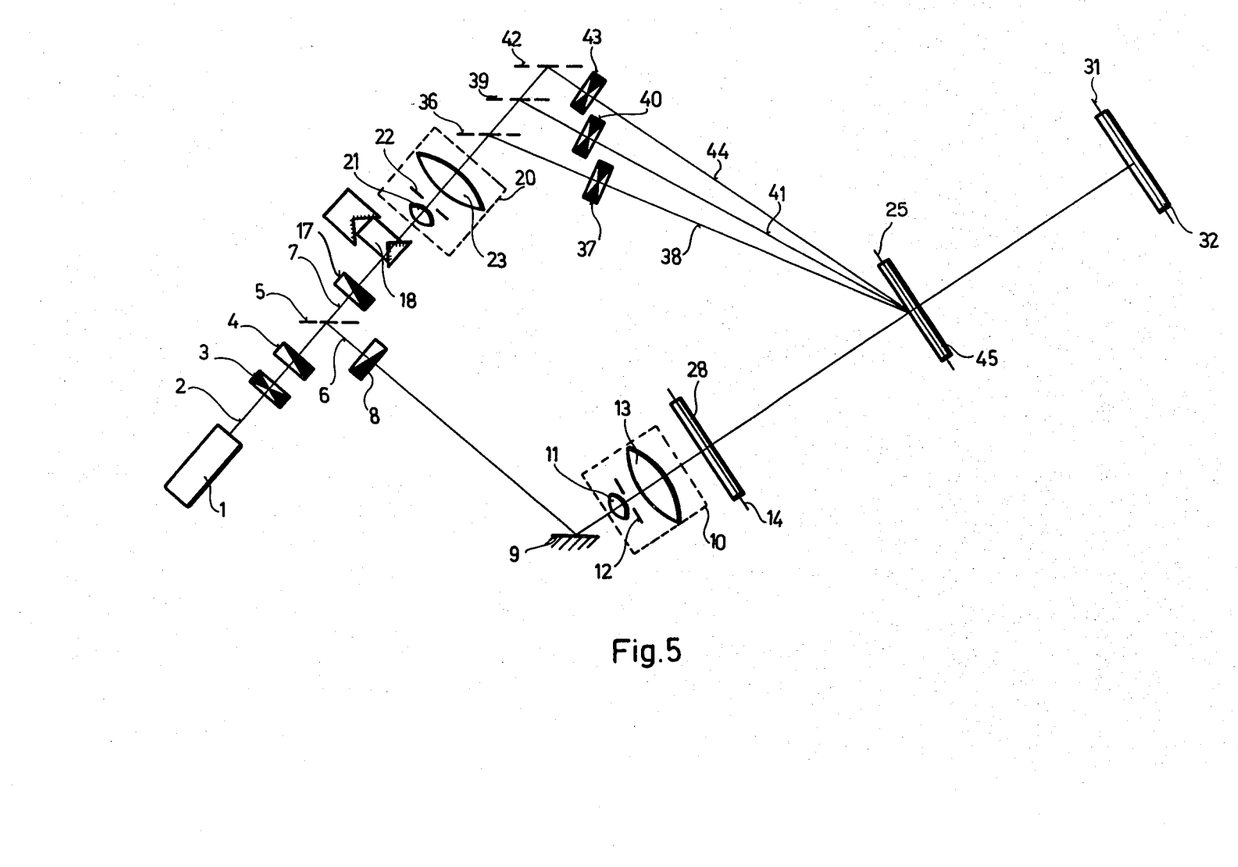
FIG. 5 is a similar view of a further embodiment with several reference beams.

FIG. 5 shows a further embodiment of the invention by which several independent reconstructed standard beams can be obtained from a single hologram by utilizing a property of the holographic recording system, namely, the fact that several standard photomasks can be recorded on the same holographic plate if the latter is illuminated at different angles by several reference beams each corresponding to an individual photomask to be recorded. The holographic recording medium 26 in the hologram plane 25 (see FIG. 1) is illuminated for example by three reference beams 38, 41 and 44 produced by first, second and third beam splitters 36, 39 and 42, respectively, which are located in the path of the undeflected beam 7. First, second and third electromechanical shutters 37, 40 and 43 disposed in the path of the reference beams ensure that at any given moment during recording only one selected reference beam can arrive at the hologram plane. To record the first hologram, the first standard photomask is placed in the object plane 14 and the first electromechanical shutter 37 is opened while the other two shutters are closed in order to ensure that only the first reference beam 38 reaches the hologram plane 25. The required intensity value is selected by means of the adjustable attenuators 8 and 17, and the electromechanical shutter 3 is opened for the time required for the exposure. In this way a holographic record can be taken from the first standard photomask.

Then the second standard photomask is placed in the object plane 14 and the record thereof is produced in the same way and on the same light-sensitive plate as in the first case with the single difference that now only the second electromechanical shutter 40 is open, allowing exclusively the second reference beam 41 to reach the hologram plane 25.

Similarly, the holograms of further standard photomasks are successively recorded on the same sensitive plate by opening the corresponding electromechanical shutter and closing the others. During the respective exposures it should be ensured that the hologram plane be illuminated at different angles by the corresponding reference beams. After taking all the holograms, the holographic recording plate is subjected to the necessary developing treatment and the resulting composite standard hologram 45 is returned to the recording position. During inspection the respective reconstructed standard beams are obtained by opening only that electromechanical shutter which was open at the time of the corresponding exposure. Alternatively, we may use only one reference beam 24 while the holographic recording plate 26 (FIG. 1) is intermittently swung about an axis which lies in the hologram plane 25 and is perpendicular to the plane determined by the standard object beam 16 and the reference beam 24. The respective holographic recordings corresponding to the different standard holograms are taken in different angular positions of the holographic recording plate 26. The desired reconstructed standard beam can be obtained by setting the superimposed standard hologram 45 (FIG. 5) in an angular position corresponding to that of the recording.

By virtue of our invention a single holographic plate can be used for recording each member of a standard mask set required e.g. for the production of an integrated circuit. This means that the complete mask set of an integrated circuit can be inspected or checked by means of a single composite standard hologram.

Under the control of the error signal obtained by the method according to the invention, the positioning of the photomask to be inspected, the adjustment of the intensity and phase conditions as well as the classification of the inspected photomasks can be automated by using conventional electronic and electromechanical means such as servo circuits, a microprocessor, a pattern analyzer etc.

The invention enables photomasks containing any number of elements, or even a single photomask element, to be compared with standard photomasks, thereby permitting the detection of random and periodic errors and a distinction between amplitude and phase errors. The images of both the standard and the inspected photomasks are obtained by beams passing along a common optical path through the central, symmetrically situated domain of the optical elements and, hence, these elements are optimally utilized. In this way a maximum resolution can be atained and no error signal results from the differences between deviating optical paths. As noted above, an automatic photomask-inspecting system can be established.

In the system of FIG. 4, one of the two cascaded lenses 33, 34 could be omitted in the projection of the inspected photomask present in plane 14 upon the receiving surface 31.

We claim:

1. A method of detecting errors on a photomask with respect to a standard photomask by subtraction technique, which comprises the steps of:
   preparing a standard hologram from said standard photomask;
   passing a reference beam of coherent radiation through said standard hologram to produce a reconstructed standard beam associated with said standard photomask;
   passing a part of said coherent radiation through a photomask to be inspected, located in a position corresponding to the location of said standard photomask during the preparation of the standard hologram, to produce an object beam from the inspected photomask;

passing said object beam through said standard hologram together with said reference beam for causing said reconstructed standard beam to interfere with said object beam to form a compound beam carrying information on both said standard and inspected photomasks;

detecting said compound beam; and adjusting the intensity ratio and contiuously varying the relative path length of the reconstructed standard beam and the object beam concurrently traversing said standard photomask during detection of said compound beam whereby phase and amplitude differences can be distinguished.

2. The method defined in claim 1 wherein the step of detecting said compound beam comprises the focusing of said compound beam upon a receiving surface to generate a difference image.

3. The method defined in claim 2 wherein the step of continuously adjusting said relative path length is accompanied by an evaluation of those spots on said difference image whose intensity remains substantially unchanged during the phase adjustment.

4. A method of detecting errors on several photomasks compared to respective standard photomasks by subtraction technique, which comprises the steps of:

preparing a standard composite hologram from said standard photomasks with the aid of respective reference beams of different angles associated with each of said standard photomasks;

passing respective reference beams of coherent radiation in sequence through said composite standard hologram to produce respective reconstructed standard beams each associated with the corresponding standard photomask;

passing a part of said coherent radiation through the respective inspected photomask simultaneously with the production of the respective reconstructed standard beam, with the respective inspected photomask located in a position corresponding to the location of the associated standard photomask during the preparation of the standard composite hologram to produce respective object beams from the inspected photomasks;

passing each object beam through said composite standard hologram simultaneously with the respective reference beam for causing each reconstructed standard beam to interfere with the corresponding object beam to form a respective compound beam carrying information on the corresponding standard and inspected photomasks;

sequentially detecting the respective compound beams; and adjusting the intensity ratio and continuously varying the relative path length of each reconstructed standard beam and the corresponding object beam concurrently traversing said composite standard photomask during detection of said compound beams whereby phase and amplitude differences can be distinguished.

5. An apparatus for detecting errors on a photomask with respect to a standard photomask, comprising:

a source of a beam of coherent radiation;

a beam splitter for dividing the beam of said source into a reference beam and an object beam traveling over two diverging paths;

deviating means for converging said diverging paths;

a carrier in the path of said object beam for alternatively holding the standard and the inspected photomask;

a holder for a standard hologram corresponding to the standard photomask located at an intersection of said converging paths;

attenuating means located in at least one of said paths for adjusting the intensity ratio between said reference and object beams;

continuously operable phase-adjusting means located in at least one of said paths for varying the relative path length of said reference and object beams; and detecting means in line with said holder for enabling the ascertainment of changes in the intensity of a compound beam generated by the simultaneous translumination of said standard hologram by said reference and object beams during operation of said attenuating and phase-adjusting means, said detecting means operating concurrently with said phase-adjusting means for enabling phase and amplitude differences to be distinguished.

6. The apparatus defined in claim 7 wherein said detecting means comprises a receiving surface beyond said holder and image-forming lens means in the paths of said object and compound beams.

7. The apparatus defined in claim 7, further comprising beam-expander means located in at least one of said paths for enlarging the beam thereof.

8. The apparatus defined in claim 5, further comprising detecting means located behind said holder in line with said object path, and focusing means for producing a compound image of said standard and inspected photomasks on said detecting means.

9. The apparatus defined in claim 5 for detecting errors on several photomasks with respect to respective standard photomasks, further comprising beam-splitter means in the path of said reference beam for selectively directing respective component beams at different angles toward said holder, and individual shutters in the paths of said component beams.

10. The apparatus defined in claim 5, further comprising shutter means located ahead of said beam splitter for timing an exposure of the standard hologram.

* * * * *